United States Patent [19]

Plöger et al.

[11] Patent Number: 4,632,826
[45] Date of Patent: Dec. 30, 1986

[54] POLISHING COMPOSITION AND DENTIFRICE

[75] Inventors: Walter Plöger, Hilden; Hans-Jürgen Klüppel, Duesseldorf; Franz Förg, Langenfeld, all of Fed. Rep. of Germany

[73] Assignee: Henkel Kommanditgesellschaft auf Aktien, Duesseldorf, Fed. Rep. of Germany

[21] Appl. No.: 752,412

[22] Filed: Jul. 3, 1985

[30] Foreign Application Priority Data

Jul. 7, 1984 [DE] Fed. Rep. of Germany ....... 3425152

[51] Int. Cl.$^4$ ............................ A61K 7/16; A61K 7/18
[52] U.S. Cl. ........................................... 424/52; 424/49
[58] Field of Search ........................................ 424/49–58

[56] References Cited

U.S. PATENT DOCUMENTS

| 3,003,919 | 10/1961 | Broge | 424/49 |
| 3,060,098 | 10/1962 | Gershon | 424/52 |
| 3,670,076 | 6/1972 | Muhler | 424/49 |
| 3,957,968 | 5/1976 | Cordon | 424/57 |
| 4,060,599 | 11/1977 | Cordon | 424/49 |
| 4,141,969 | 2/1979 | Mitchell | 424/52 |
| 4,144,322 | 3/1979 | Cordon et al. | 424/49 |
| 4,153,680 | 5/1979 | Seybert | 424/49 |
| 4,160,022 | 7/1979 | Delaney et al. | 424/52 |
| 4,174,387 | 11/1979 | Cordon et al. | 424/52 |
| 4,412,983 | 11/1983 | Mitchell . | |

Primary Examiner—Shep K. Rose
Attorney, Agent, or Firm—Ernest G. Szoke; Henry E. Millson, Jr.

[57] ABSTRACT

A composition of matter useful as a polishing agent combination in a dentifrice, such as a toothpaste. A silica polishing agent is combined with a weakly calcined alumina polishing agent. Preferably, the weakly calcined alumina contains about 50%–90% by weight of alpha aluminum oxide and about 10%–50% by weight of gamma aluminum oxide. Preferably, the silica polishing agent is selected from the group consisting of precipitated silica and silica gel.

25 Claims, No Drawings

POLISHING COMPOSITION AND DENTIFRICE

BACKGROUND OF THE INVENTION

1. Field of the Invention

This invention relates to a composition of matter useful as a polishing agent in a dentifrice and to a dentifrice, preferably a toothpaste, which effectively cleans and polishes teeth without a high degree of abrasion and scratching.

2. Description of the Relevant Art

Dentifrices are used to clean teeth. In particular, a toothpaste is preferably brushed daily against the teeth with a toothbrush. A toothpaste aids in the removal of food particles, the removal of discoloration caused by substances such as tobacco or tea, and the removal of firmly adhering bacterial films, referred to as plaque, from the surface of teeth. In addition to removing substances from the surface of teeth, toothpastes also polish teeth. Both cleaning and polishing are effected by (1) abrasive substances, referred to herein as polishes, which are present in the toothpaste and, (2) to a lesser extent, surfactants which are contained in the toothpaste.

To achieve cleaning and polishing, the polishes have to provide a certain degree of abrasiveness with respect to the surface of the teeth. It is important, however, that abrasiveness with respect to dental enamel and dentine be at an acceptably low level to prevent the surface of the teeth from being damaged by the daily use of the toothpaste. Not only should the polishes in the toothpaste avoid producing any deep scratches on the surface of the teeth, but also the polishes should in fact assist in smoothing out any roughness there may be on the surface of the teeth.

A suitable polish should of course also be compatible with the other components of the toothpaste. It should lend itself to processing with water, humectants and consistency regulators to form a ductile paste readily dispensable from tubes or dispensers and should not adversely affect known caries inhibitors, for example fluoride carriers, such as NaF or Na monofluorophosphate, even in the event of prolonged storage.

As illustrated in U.S. Pat. No. 3,957,968, toothpastes containing a combination of alpha-aluminum oxide (corundum) and a polish having a Mohs hardness of less than about 6 are said to have good cleaning and polishing effects. Alpha-aluminum oxide, however, has a relatively strong abrasive effect on dental enamel. To reduce the enamel abrasion, certain calcium, magnesium or sodium salts have been added to a dentifrice containing alpha-aluminum oxide polishes and a hydrated silicious abrasive, with or without raising the pH of the dentifrice to a value above 7, as shown in U.S. Pat. No. 4,144,322. According to U.S. Pat. No. 4,060,599, alpha-aluminum oxide is used in a mean ultimate crystalline particle size of about 1 to 2 microns.

The above-mentioned measures have not completely solved the problem of the excessive abrasion of dental enamel and the excessive scratching effects associated with known polishes. Workers in the art have continued to search for dentifrices containing polishing agents which have reduced abrasion of dental enamel and reduced scratching effects.

Accordingly, an object of the present invention is to provide suitable polishing agents or polishing agent combinations which, although achieving an optimal cleaning and decoloring effect on the surface of teeth, can have only a mild abrasive and scratching effect.

Another object of the invention is to provide a suitable carrier for such polishing agents which makes it possible to produce a toothpaste that can have (1) suitable consistency for dispensing from tubes and dispensers and (2) high stability against changes in consistency during storage.

Finally, an object of the present invention is to find a toothpaste which, by virtue of its overall composition, can satisfy to a high degree the various demands made of a modern dental care preparation.

DESCRIPTION OF THE INVENTION

To achieve the foregoing objectives, there is provided a polishing agent combination, useful in a dentifrice, such as a toothpaste, comprising a silica polishing agent and a weakly calcined alumina polishing agent.

A preferred form of the present invention is a toothpaste containing from about 15% to 30%, preferably 15% to 20%, by weight of a polishing agent combination of at least one silica polish (A) which is one or more of a silica gel and a precipitated silica, and at least one weakly calcined alumina polish (B) comprising from about 10% to 50% by weight of gamma-aluminum oxide ($\gamma$-$Al_2O_3$) and from about 50% to 90% by weight of alpha-aluminum oxide ($\alpha$-$Al_2O_3$); from about 70% to 85% by weight of a carrier comprising water, at least one humectant and at least one consistency regulator; and up to about 5% by weight of other standard toothpaste additives, the ratio by weight between the polishes (A) and (B) amounting to about 100:(0.8–39), preferably about 100:(2–15), more preferably 100:(2–6).

Aluminum oxide polishes having various degrees of calcination, finenesses and powder densities are commercially available. In particular, suitable weakly calcined aluminas for use in accordance with the invention are available commercially. For instance, Giulini-Chemie provides a weakly calcined alumina suitable for use in the present invention.

Alternatively, weakly calcined alumina for use in accordance with the invention may be produced by calcination from aluminum hydroxide. Aluminum hydroxide is converted by calcination into $\alpha$-$Al_2O_3$ which is thermodynamically stable at temperatures above 1200° C. The thermodynamically unstable forms of $Al_2O_3$ occurring at temperatures between 400° and 1000° C. are known as gamma forms (cf. Ullman, *Encyclopaedie der Technischen Chemie*, 4th ed. (1974), Vol. 7, p. 298). The degree of calcination, i.e. conversion into the thermodynamically stable $\alpha$-$Al_2O_3$, may be adjusted as required in dependence upon the calcination temperature and time. Mild or weak calcination gives an alumina of which the $\alpha$-$Al_2O_3$ content is lower and the $\gamma$-$Al_2O_3$ content is higher compared to strong calcination. As the calcination temperature and the calcination time increase, the amount of $\alpha$-$Al_2O_3$ increases and the amount of $\gamma$-$Al_2O_3$ decreases. Weakly calcined aluminas thus have more $\gamma$-$Al_2O_3$ than do strongly calcined aluminas and are distinguished from pure $\alpha$-$Al_2O_3$ by a lower hardness of the agglomerate, a higher specific surface area and larger pore volumes.

More specifically, the weakly calcined alumina of the present invention preferably has a gamma-aluminum oxide ($\gamma$-$Al_2O_3$) content of approximately 10%–50% by weight, preferably 15%–25% by weight, more preferably 20% by weight, of the total aluminum oxide and an alpha-aluminum oxide ($\alpha$-$Al_2O_3$) content of approximately 50% to 90% by weight, preferably 75% to 85% by weight, more preferably 80% by weight, of the total aluminum oxide. The weakly calcined aluminum oxide of the present invention also preferably has an average agglomerate size of less than about 20µ, an average primary crystal size of from about 0.5 to about 1.5µ and a powder density of from about 500 g/l to about 600 g/l.

Dentine abrasion value (RDA) of a particular substance can readily be determined by one skilled in the art. See e.g., U.S. Pat. No. 4,153,680, column 4, lines 65–68 and column 5, lines 1–35; U.S. Pat. No. 4,144,322, column 5, lines 52–54; U.S. Pat. No. 3,957,968, column 2, lines 25–27; and U.S. Pat. No. 4,060,599, column 3, lines 7–9. The RDA of the weakly calcined alumina containing about 10% to 50% by weight of $\gamma Al_2O_3$, used in accordance with the invention, amounts to only about 30% to 60% of the RDA of a strongly calcined, pure $\alpha$-$Al_2O_3$ (as measured in a standard toothpaste containing about 20% by weight of alumina as the sole polish).

In contrast to $\alpha$-$Al_2O_3$, $\gamma$-$Al_2O_3$ can be dyed red with an aqueous-ammoniacal solution of Alizarin S acid (1,2-dihydroxy-9,10-anthraquinone-4-sulfonic acid), a commercially available product. The degree of dyeability may be used as a measure of the degree of calcination or of the percentage of $\gamma$-$Al_2O_3$ in a calcined alumina.

For example, approximately 1 g of $Al_2O_3$, 10 ml of a solution of 2 g/l of Alizarin S acid in water and 3 drops of an aqueous 10% by weight solution of $NH_3$ are introduced into a test tube and briefly boiled. The $Al_2O_3$ is filtered off, washed, dried and examined under a microscope or evaluated by colorimetry. A suitable weakly calcined alumina containing from 10% to 50% by weight of $\gamma$-$Al_2O_3$ will be dyed pale to deep pink by this method.

A variety of silica polishes may be used in conjunction with weakly calcinated aluminum oxide in accordance with the present invention. For example, representative silica polishes include silica gels which either are available commercially from, for example, W. R. Grace & Co., or can be obtained by reacting sodium silicate solutions with strong aqueous mineral acids to form a hydrosol, aging the hydrosol thus formed to form the hydrogel, washing and drying.

If drying is carried out under mild conditions to achieve water contents of from about 15% to 35% by weight, silica hydrogels such as those described in U.S. Pat. No. 4,153,680, the disclosure of which is specifically incorporated by reference herein, are obtained and can be used in accordance with the present invention. Silica hydrogels are preferred silica polishes for the dentrifices produced in accordance with the present invention. Particularly preferred hydrogels have a water content of from about 15% to 35% by weight and a particle size of from about 0.5µ to 30µ, in which at least 80% by weight of the primary particles are smaller than 5µ.

Silica xerogels are also useful in the present invention and either are available commercially from, for example, W. R. Grace & Co., or can be obtained by drying the water content of the hydrogel below 15% by weight which results in irreversible shrinkage of the previously loose structure of the hydrogel to the compact structure of a xerogel. Silica xerogels useful in the present invention are also described in U.S. Pat. No. 3,538,230, the disclosure of which is specifically incorporated by reference herein.

Silica xerogels have greater hardness and abrasiveness than do silica hydrogels. To achieve the required polishing effect, silica xerogels are thus suitable in smaller proportions as a component of the polishing agent combination according to the invention. The silica xerogels can be used in amounts of about 8.3 to 25%, preferably about 23 to 29.4% by weight, based on the weight of the silica hydrogel used.

Another example of suitable silica polishes includes the precipitated silicas. Precipitated silicas are either available commercially from, for example, Degussa AG or can be obtained by precipitating silica from dilute alkali silicate solutions by the addition of strong acids under conditions where aggregation to the sol and gel cannot occur. Suitable processes for producing precipitated silicas are described, for example, in German Offenlegungsschrift 25 22 486 and 31 14 493.

A particularly suitable precipitated silica is the precipitated silica produced in accordance with German Offenlegungsschrift 31 14 493 and which has a BET surface of from 15 to 110 m$^2$/g, a particle size of from about 0.5µ to 30µ (at least 80% by weight of the primary particles should be smaller than 5µ) and a viscosity in the form of a 30% glycerin-water (1:1) dispersion of from 30 to 60 Pa.s (20° C.).

By virtue of the special polishing agent combination described above, toothpastes in accordance with the present invention can have excellent cleaning power, even with respect to discoloration caused by tea and nicotine. At the same time, the toothpastes of the present invention can achieve a high polishing effect (smoothing out any roughness present) with only moderate abrasion of dentine and enamel. Despite the presence of a relatively hard polishing component (the weakly calcined alumina), the toothpastes according to the invention can have practically no scratching effect. These results are surprising because previous experience had shown that a high cleaning and/or polishing effect could only be obtained at the price of relatively high dentine or enamel abrasion and/or relatively high scratching values.

For special dentifrices, such as children's tooth creams, smoker's tooth creams, and antistaining tooth creams which are only occasionally used, the required level of cleaning and polishing and of tolerable abrasion values may be entirely different. However, toothpastes according to the invention can produce very little abrasion compared to the cleaning and polishing effect achieved. Special polishing and abrasion values may be adjusted, on the one hand, through the degree of calcination of the alumina, i.e., the percentage contents of gamma-aluminum oxide and alpha-aluminum oxide in the polish combination, and, on the other hand, through the use of different silica qualities and mixtures thereof.

To produce a dentifrice known as a smoker's tooth cream suitable for daily use to combat staining caused by the consumption of tobacco and also of tea, it has proved to be particularly effective in terms of cleaning to use a polishing agent combination of:

from about 12% to 20%, preferably 13% to 17%, by weight of a silica hydrogel;

from about 1% to 5%, preferably 3% to 5%, by weight of silica xerogel; and from about 0.2% to 5%, preferably 1% to 3%, by weight of a weakly calcined alumina containing from 10% to 50%, preferably 15%–25%, by weight of $\gamma$-$Al_2O_3$ and from 50% to 90%, preferably, 75% to 85%, by weight of α-Al$_2$O$_3$, all weights being based on the toothpaste as a whole.

A representative carrier for the dentifrices or toothpastes according to the invention, which makes it possible to produce pastes of suitable consistency for packing in and dispensing from tubes and dispensers on the basis of the polishing agent combination according to the invention, is a combination of water, humectants and consistency regulators. Representative humectants include glycerin, sorbitol, xylitol, propylene glycols, polyethylene glycols, particularly those having average molecular weights of from 200 to 800.

Representative consistency regulators (or binders) are, for example, natural and/or synthetic water-soluble polymers, such as carrageenates, tragacanth, starch and starch ethers, cellulose ethers such as, for example, methyl-hydroxy-propyl cellulose, quar gum, gum arabic, agar agar, xanthan gum, carob bean flour, pectins, water-soluble carboxyvinyl polymers (for example Carbopol ® types), polyvinyl alcohol, polyvinyl pyrrolidone, and polyethylene glycols, particularly those having molecular weights of from 1500 to 1,000,000.

Other representative substances suitable for regulating viscosity are, for example, layer silicates such as, for example, montmorillonite clays, colloidal thickening silicas such as, for example, Aerosil silicas or pyrogenic silicas. A carrier particularly suitable for the production of toothpastes containing the polishing agent combination according to the invention contains:

from about 25% to 35% by weight of water;
from about 25% to 35% by weight of sorbitol;
from about 10% to 15% by weight of glycerin;
from about 2% to 10% by weight of polyethylene glycol (average molecular weight 200–800);
from about 0.1% to 0.5% by weight of carboxymethyl cellulose; and
from about 1% to 3% by weight of thickening silica (for example Syloblanc ® 34 silica), all weights being based on the toothpaste as a whole.

Other standard dentifrice or toothpaste ingredients, which together may preferably constitute up to about 5% by weight of the dentifrice or toothpaste as a whole, may be used. Such ingredients include, for example, surfactants for supporting the cleaning effect and, optionally, for the development of foam during brushing and for stablizing the dispersion of the polishing components in the carrier. The surfactants may be anionic, cationic, nonionic or ampholytic in nature. Representative surfactants include, for example, linear sodium alkyl sulfates containing from 12 to 18 carbon atoms in the alkyl group. These substances also have an enzyme-inhibiting effect on the bacterial metabolism of plaque. Other suitable surfactants are alkali salts, preferably sodium salts, of alkyl polyglycol ether sulfate containing from 12 to 16 carbon atoms in the linear alkyl group and from 2 to 6 glycol ether groups in the molecule, of alkyl (C$_{12-16}$) benzene sulfonate, of linear alkane (C$_{12-18}$) sulfonate, of sulfosuccinic acid monoalkyl (C$_{12-18}$) esters, of sulfated fatty acid monoglycerides, sulfated fatty acid alkanolamides, sulfoacetic acid alkyl (C$_{12-16}$) esters, acyl sarcosines, acyl taurides and acyl isothionates with, in each case, from 8 to 18 carbon atoms in the acyl group. It is also possible to use nonionic surfactants, for example ethoxylates of fatty acid mono- and diglycerides, of fatty acid sorbitan esters and ethylene oxide/propylene oxide block polymers.

Other standard toothpaste ingredients which include preservatives and microbicides such as, for example, p-hydroxybenzoic acid methyl, ethyl or propyl ester, sodium sorbate, sodium benzoate, bromochlorophene, phenyl salicylic acid ester, thymol, and guanidines, biguanidines and amines such as:

N$^o$-(4-chlorobenzyl)-N$^5$-2,4-(dichlorobenzyl) biguanide;
p-chlorophenyl biguanide;
4-chlorobenzhydryl biguanide;
4-chlorobenzhydrylguanylurea;
N$^1$-3-lauroxypropyl-N$^5$-p-chlorobenzylbiguanide;
1-(lauryldimethylammonium)-8-(p-chlorobenzyldimethylammonium) octane dichloride;
5,6-dichloro-2-guanidinobenzimidazole;
N$^1$-p-chlorophenyl-N$^5$-laurylbiguanide;
5-amino-1, 3-bis (2-ethylhexyl)-5-methylhexahydropyrimidine; and their non-toxic acid addition salts.

anti-tartar agents, for example organophosphonates, such as the sodium salts of 1-hydroxyethane-1,1-diphosphonic acid, 1-phosphonopropane-1,2,3-tricarboxylic acid and other phosphonic acids of the type described, for example, in U.S. Pat. No. 3,488,419, in German Offenlegungsschrift No. 22 24 430 and in German Offenlegungsschrift No. 23 4 196, caries inhibitors, such as, for example, sodium fluoride, sodium monofluorophosphate, and tin fluoride;

sweeteners, such as, for example, saccharin sodium, sodium cyclamate, sucrose, lactose, maltose, fructose;

flavorings such as, for example, peppermint oil, spearmint oil, eucalyptus oil, anise seed oil, fennel oil, caraway oil, methyl acetate, cinnamic aldehyde, anethol, vanillin, thymol and also mixtures of these and other natural and synthetic flavorings;

pigments such as, for example, titanium dioxide;
dyes;

buffers such as, for example, primary, secondary or tertiary alkali phosphates or citric acid/sodium citrate; and wound-healing and inflammation-inhibiting substances such as, for example, allantoin, urea and also azulene, camomile, and acetyl salicylic acid derivatives.

The dentifrices according to the invention preferably contain:

from about 0.5% to 3.0% by weight of anionic surfactants, such as, for example, sodium lauryl sulfate;
from about 0.1% to 1.0% by weight of sodium fluoride and/or sodium monofluorophosphate; and
from about 0.1% to 0.3% by weight of saccharin-sodium.

The following Examples are intended to illustrate the present invention without limiting it in any way:

| Tooth cream | Examples | |
|---|---|---|
| | I[8] | II[8] |
| Precipitated silica[1] | 18 | — |
| Silica hydrogel[2] | — | 15 |
| Silica xerogel[3] | — | 4.0 |
| Weakly calcined alumina[4] | 1.0 | 1.0 |
| Thickening silica (pyrogenic)[5] | 0.8 | 0.5 |
| Sorbitol | 17.5 | 17.5 |
| Glycerin | 17.5 | 17.5 |
| Carboxymethyl cellulose[6] | 0.9 | 0.6 |
| Sodium lauryl sulfate[7] | 2.0 | 2.0 |
| Sodium fluoride | 0.22 | 0.22 |
| Saccharin-sodium | 0.2 | 0.2 |
| Flavoring oils | 1.0 | 1.0 |

| | Examples | |
|---|---|---|
| Tooth cream | I[8] | II[8] |
| Water, preservative | add to 100 | add to 100 |

[1]Sident ® 12 DS, DEGUSSA
[2]Syloblanc ® 84, GRACE
[3]Syloblanc ® 81, GRACE
[4]Polishing alumina P10 ultrafine, Giulini-Chemie
[5]Aerosil ® 200, DEGUSSA
[6]Relatin ® 100 S, HENKEL KGaA
[7]Texapon ® K 1296, HENKEL KGaA
[8]All components except water are expressed in percent by weight, based on the total composition. The percent of water in each example is 100 minus the total weight percent of all other components.

What is claimed is:

1. A tooth cream, suitable for daily use, for removing stain caused by the consumption of tobacco, tea and mixtures thereof from the surfaces of teeth and to polish and clean the surface of said teeth, without producing any deep scratches or damage by daily use to the surfaces of the teeth, said tooth cream containing, as the essential stain removing component dentifrice polishing agent consisting essentially of
   (a) 100 parts by weight of silica polishing agent consisting essentially of at least one of
      (i) silica hydrogel, and
      (ii) precipitated silica; and
   (b) 2 to 15 parts by weight of weakly calcined alumina polishing agent consisting essentially of
      (i) 10 to 50% by weight of gamma aluminum oxide and
      (ii) 50 to 90% by weight of alpha aluminum oxide, 2. The dentifrice polishing agent of claim 1 wherein said silica polishing agent consists essentially of at least one of
      (i) silica hydrogel which contains about 15 to 35% water, based on weight of the silica hydrogel, and
      (ii) precipitated silica which has a BET surface area of from about 15 to 110 m$^2$/g.

3. The dentifrice polishing agent of claim 1 wherein said weakly calcined alumina polishing agent consists essentially of aluminum oxide particles which have an average agglomerate size of less than about 20 microns, an average primary crystal size of from about 0.5 to 1.5 microns and a powder density of from about 500 g/l to 600 g/l.

4. A tooth cream, suitable for daily use, for removing stain caused by the consumption of tobacco, tea and mixtures thereof from the surfaces of teeth and to polish and clean the surface of said teeth, without producing any deep scratches or damage by daily use to the surfaces of the teeth, said tooth cream containing, as the essential stain removing component dentifrice polishing agent consisting essentially of
   (a) 100 parts by weight of silica polishing agent consisting essentially of at least one of
      (i) silica hydrogel which contains about 15 to 35% water, based on weight of the silica hydrogel, and which has a particle size of from about 0.5 to 30 microns, wherein at least 80% by weight of primary particles of said hydrogel are smaller than 5 microns; and
      (ii) precipitated silica which has a BET surface area of from about 15 to 100 m$^2$/g and a particle size of from about 0.5 to 30 microns, wherein at least 80% by weight of the primary particles of said precipitated silica are smaller than about 5 microns, and wherein said precipitated silica has a viscosity in the form of a 30% glycerin-water (1:1) dispersion of from about 30 to 60 Pa.s (20° C.); and
   (b) 2 to 15 parts by weight of a weakly calcined alumina polishing agent consisting essentially of
      (i) 10 to 50% by weight of gamma aluminium oxide and
      (ii) 50 to 90% by weight of alpha aluminum oxide, wherein said weakly calcined aluminum oxide has an average agglomerate size of less than about 20 microns, an average primary crystal size of from about 0.5 to 1.5 microns and a powder density of from about 500 g/l to about 600 g/l.

5. The dentifrice polishing agent of claim 1 wherein said silica polishing agent consists essentially of silica hydrogel.

6. The dentifrice polishing agent of claim 1 wherein said silica polishing agent consists essentially of silica hydrogel and about 8.3 to 25% by weight of silica xerogel based on weight of silica hydrogel.

7. The dentifrice polishing agent of claim 1 wherein said silica polishing agent consists essentially of precipitated silica.

8. The dentifrice polishing agent of claim 1 wherein said weakly calcined alumina polishing agent consists essentially of
   (i) 15 to 25% by weight of gamma aluminum oxide and
   (ii) 75 to 85% by weight of alpha aluminum oxide.

9. The dentifrice polishing agent of claim 8 wherein said weakly calcined alumina polishing agent consists essentially of
   (i) about 20% by weight of gamma aluminum oxide and
   (ii) about 80% by weight of alpha aluminum oxide.

10. A tooth cream, suitable for daily use, for removing stain caused by the consumption of tobacco, tea and mixtures thereof from the surfaces of teeth and to polish and clean the surface of said teeth, without producing any deep scratches or damage by daily use to the surfaces of the teeth, said tooth cream containing, as the essential stain removing component dentifrice composition comprising a polishing agent which consists essentially of
    (a) 15 to 30% by weight of the dentifrice polishing agent of claim 1; and
    (b) 70 to 85% by weight of a dentifrice carrier.

11. A tooth cream, suitable for daily use, for removing stain caused by the consumption of tobacco, tea and mixtures thereof from the surfaces of teeth and to polish and clean the surface of said teeth, without producing any deep scratches or damage by daily use to the surfaces of the teeth, said tooth cream containing, as the essential stain removing component dentifrice composition comprising a polishing agent which consists essentially of
    (a) 15 to 20% by weight of the dentifrice polishing agent of claim 4; and
    (b) 80 to 85% by weight of a dentifrice carrier.

12. The dentifrice composition of claim 10 wherein the dentifrice carrier comprises water, at least one humectant and at least one consistency regulator and 0 to 5% by weight of one or more conventional dentifrice additives.

13. The dentifrice composition of claim 11 wherein the dentifrice carrier comprises water, at least one humectant and at least one consistency regulator and 0 to 5% by weight of one or more conventional dentifrice additives.

14. The dentifrice composition of claim 10 wherein said carrier comprises
    (a) 25 to 35% by weight water;
    (b) 25 to 35% by weight sorbitol;.
    (c) 10 to 15% by weight glycerin;
    (d) 2 to 10% by weight polyethylene glycol (average molecular weight 200–800);
    (e) 0.1 to 0.5% by weight carboxymethyl cellulose; and
    (f) 1 to 3% weight thickening silica, wherein all percentages by weight are based on the dentifrice as a whole.

15. The dentifrice composition of claim 14 wherein said carrier comprises
    (a) 0.5 to 3.0% by weight of at least one anionic surfactant;
    (b) 0.1 to 1.0% by weight of at least one of sodium fluoride and sodium monofluorophosphate; and
    (c) 0.1 to 0.3% by weight of saccharin-sodium.

16. The dentifrice composition of claim 14 wherein said dentifrice is a tooth paste.

17. The dentifrice composition of claim 15 wherein said dentifrice is a tooth paste.

18. A tooth cream, suitable for daily use, for removing stain caused by the consumption of tobacco, tea and mixtures thereof from the surfaces of teeth and to polish and clean the surface of said teeth, without producing any deep scratches or damage by daily use to the surfaces of the teeth, said tooth cream containing, as the essential stain removing component dentifrice composition comprising a polishing agent which consists essentially of
    (a) 12 to 20% by weight of the silica hydrogel of claim 1 and
    (b) 0.2 to 5% by weight of the weakly calcined alumina polishing agent of claim 1, based on weight of the dentifrice as a whole.

19. A tooth cream, suitable for daily use, for removing stain caused by the consumption of tobacco, tea and mixtures thereof from the surfaces of teeth and to polish and clean the surface of said teeth, without producing any deep scratches or damage by daily use to the surfaces of the teeth, said tooth cream containing, as the essential stain removing component dentifrice composition comprising of a polishing agent which consists essentially of
    (a) 13 to 17% by weight of the silica hydrogel of claim 4 and
    (b) 1 to 3% by weight of the weakly calcined alumina polishing agent of claim 4, based on weight of the dentifrice as a whole.

20. The dentifrice composition of claim 18 comprising 1 to 5% by weight of silica xerogel.

21. The dentifrice composition of claim 19 comprising 3 to 5% by weight of silica xerogel.

22. The dentifrice composition of claim 18 comprising a dentifrice carrier which comprises
    (a) 25 to 35% by weight water;
    (b) 25 to 35% by weight sorbitol;
    (c) 10 to 15% by weight glycerin;
    (d) 2 to 10% by weight polyethylene glycol (average molecular weight 200–800);
    (e) 0.1 to 0.5% by weight carboxymethyl cellulose; and
    (f) 1 to 3% by weight thickening silica, wherein all percentages by weight are based on the dentifrice as a whole.

23. The dentifrice composition of claim 22 comprising a dentifrice carrier which comprises
    (a) 0.5 to 3.0% by weight of at least one anionic surfactant;
    (b) 0.1 to 1.0% by weight of at least one of sodium fluoride and sodium monofluorophosphate; and
    (c) 0.1.to 0.3% by weight of saccharin-sodium.

24. The dentifrice composition of claim 19 comprising a dentifrice carrier which comprises
    (a) 25 to 35% by weight water;
    (b) 25 to 35% by weight sorbitol;
    (c) 10 to 15% by weight glycerin;
    (d) 2 to 10% by weight polyethylene glycol (average molecular weight 200–800);
    (e) 0.1 to 0.5% by weight carboxymethyl cellulose; and
    (f) 1 to 3% by weight thickening silica, wherein all percentages by weight are based on the dentifrice as a whole.

25. The dentifrice composition of claim 24 comprising a dentifrice carrier which comprises
    (a) 0.5 to 3.0% by weight of at least one amionic surfactant;
    (b) 0.1 to 1.0% by weight of at least one of sodium flouride and sodium monofluoridephosphate;
    (c) 0.1 to 0.3% by weight of saccharin-sodium.

* * * * *